United States Patent
Kraft et al.

(10) Patent No.: US 10,876,225 B2
(45) Date of Patent: Dec. 29, 2020

(54) POLYSACCHARIDE FIBERS AND METHOD FOR PRODUCING SAME

(71) Applicant: DUPONT INDUSTRIAL BIOSCIENCES USA, LLC, Wilmington, DE (US)

(72) Inventors: Gregor Kraft, Timelkam (AT); Gert Kroner, Seewalchen (AT); Thomas Röder, Vöcklabruck (AT); Heinrich Firgo, Vöcklabruck (AT)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 151 days.

(21) Appl. No.: 15/980,140

(22) Filed: May 15, 2018

(65) Prior Publication Data

US 2018/0258557 A1   Sep. 13, 2018

Related U.S. Application Data

(63) Continuation of application No. 14/899,197, filed as application No. PCT/AT2014/000123 on Jun. 13, 2014, now abandoned.

(30) Foreign Application Priority Data

Jun. 17, 2013   (AT) .................................. A 485/2013

(51) Int. Cl.
| | | |
|---|---|---|
| *D01F 2/06* | (2006.01) | |
| *C08B 37/00* | (2006.01) | |
| *D21H 13/08* | (2006.01) | |
| *D01D 5/06* | (2006.01) | |
| *C08L 5/00* | (2006.01) | |
| *D21H 13/00* | (2006.01) | |
| *D01F 2/08* | (2006.01) | |
| *D01F 9/00* | (2006.01) | |
| *A61L 15/28* | (2006.01) | |
| *D04H 1/28* | (2012.01) | |
| *D04H 3/013* | (2012.01) | |

(52) U.S. Cl.
CPC ................ *D01F 2/06* (2013.01); *A61L 15/28* (2013.01); *C08B 37/0009* (2013.01); *C08L 5/00* (2013.01); *D01D 5/06* (2013.01); *D01F 2/08* (2013.01); *D01F 9/00* (2013.01); *D21H 13/00* (2013.01); *D21H 13/08* (2013.01); *D04H 1/28* (2013.01); *D04H 3/013* (2013.01)

(58) Field of Classification Search
CPC .......... D21H 13/02; D21H 13/08; D01F 2/02; D01F 2/06; D01F 2/08; C08L 1/02; C08L 1/24; C08L 5/02; C08B 37/0009; C08B 37/0021; D01D 5/06
USPC ....... 162/157.7; 264/188, 189, 178 F, 178 R, 264/205, 207; 536/123.1, 123.12
See application file for complete search history.

(56) References Cited

U.S. PATENT DOCUMENTS

| | | | | |
|---|---|---|---|---|
| 6,846,924 B1 * | 1/2005 | Malmgren | ................ | D01F 2/28 536/102 |
| 2013/0313737 A1 * | 11/2013 | O'Brien | .................... | D01F 9/00 264/13 |

* cited by examiner

*Primary Examiner* — Eric Hug

(57) ABSTRACT

The present invention relates to a method for the production of polysaccharide fibers which contain α(1→3)-glucan as a fiber-forming substance, as well as to the fibers made thereby, and to their use.

7 Claims, No Drawings

POLYSACCHARIDE FIBERS AND METHOD FOR PRODUCING SAME

The present application is a continuation of U.S. patent application Ser. No. 14/899,197, published as US 2016-0138195 A1 filed Dec. 17, 2015, which is a national-stage entry under 35 U.S.C. § 371 of International Patent Application No. PCT/AT2014/000123, published as WO 2014/201482, filed Jun. 13, 2014, which claims priority to Austrian Patent Application No. A 485-2013, filed Jun. 17, 2013, the entire disclosure of each of which is incorporated by reference herein.

BACKGROUND OF THE INVENTION

The present invention relates to a method for the production of polysaccharide fibers which contain α(1→3)-glucan as a fiber-forming material, as well as to the fibers made thereby, and to their use.

Polysaccharides are becoming increasingly important, as they are materials that can be obtained from renewable raw materials. One of the most frequently occurring polysaccharides is cellulose. Cotton fibers, which consist almost exclusively of cellulose, are an example of the significance of polysaccharides. However, also materials obtained from other cellulosic raw materials, e.g., cellulosic synthetic fibers, are continuing to gain in importance.

The generic names "viscose fibers" and "modal fibers" were assigned by BISFA (the International Bureau for the Standardization of Man-made Fibers) to cellulose fibers produced through chemical derivatization of cellulose with the help of an aqueous sodium hydroxide solution and carbon disulfide ($CS_2$).

The name "modal fiber" is a generic term which, as defined by BISFA, stands for a cellulose fiber having a defined high wet strength and an also defined high wet modulus (i.e., the force required to produce an elongation of the fiber of 5% in its wet state).

However, to date, only one method for the large-scale production of fibers of the viscose and modal types has gained acceptance, namely, the viscose process and variations thereof.

From many patent specifications and other publications, it has generally been known to those skilled in the art for quite some time how this process is carried out. A method for the production of modal fibers is, for example, known from AT 287.905 B.

In the known viscose processes, CS2 has 2 essential functions:
1. Reaction with alkali cellulose into a xanthogenate that is soluble in alkaline solution;
2. "Effect in spin bath".

In the viscose spin bath, colloid-chemical (coagulation of the sodium cellulose xanthogenate) and chemical (decomposition of the xanthogenate into hydrate cellulose) processes take place in parallel. Both are influenced by the $CS_2$ used.

Compared to the new resource-sparing and environmentally friendly lyocell process, the viscose process has a serious disadvantage: the use of large quantities of $CS_2$ and aqueous sodium hydroxide solution. This problem exists to an even greater degree in the production of modal fibers. In the following text, the terms viscose process and viscose fiber are used to cover all viscose processes and variations thereof, including the modal process, as well as the fibers produced thereby.

The cellulosic raw material that has been used so far in the viscose process is pulp obtained primarily from wood. Despite numerous studies, it has yet not been possible to develop a viscose-technology-based method that would allow to significantly reduce the use of $CS_2$ and NaOH, respectively.

U.S. Pat. No. 7,000,000 describes fibers obtained by spinning a solution of polysaccharides which substantially consist of repeating hexose units linked via α(1→3)-glycosidic bonds. These polysaccharides can be produced by bringing an aqueous solution of saccharose into contact with glucosyltransferase (GtfJ), isolated from *Streptococcus salivarius* (Simpson et al., Microbiology, vol. 41, pp 1451-1460 (1995)). As used in this context, "substantially" means that within the polysaccharide chains there may exist occasional defective locations where other bond configurations may occur. For the purposes of the present invention, these polysaccharides shall be referred to as "α(1→3)-glucan".

U.S. Pat. No. 7,000,000 first discloses possibilities for the enzymatic production of α(1→3)-glucan from monosaccharides. In this way, relatively short-chained polysaccharides can be produced without the loss of monomer units, as the polymer chains are built from the monomer units. Contrary to the production of short-chained cellulose molecules, the production of α(1→3)-glucan keeps getting less expensive the shorter the polymer chains are, as in that case only a short residence time in the reactors will be required.

According to U.S. Pat. No. 7,000,000, the α(1→3)-glucan is to be derivatized, preferably acetylated. Preferably, the solvent is an organic acid, an organic halogen compound, a fluorinated alcohol, or a mixture of such components. These solvents are costly and complex to regenerate.

However, studies have also shown α(1→3)-glucans to be soluble in a diluted aqueous sodium hydroxide solution (approx. 4 to 5.5%).

WO 2013/052730 A1 discloses fibers that have α(1→3)-glucan as a fiber-forming substance and are produced by spinning according to the so-called amine-oxide process using NMMO as a solvent. The amine-oxide process is designed in a way that is fundamentally different from the viscose or modal processes and requires an entirely different production plant. A viscose production plant cannot be converted for the amine-oxide process just by simple modifications.

OBJECT

In view of such prior art, the object was therefore to provide an alternative method for the production of a polysaccharide fiber, which renders it possible to significantly reduce the used quantities of $CS_2$ and aqueous sodium hydroxide solution per fiber unit produced.

DESCRIPTION OF THE INVENTION

The above described object is solved by a new method for the production of a polysaccharide fiber whose fiber-forming substance is α(1→3)-glucan, the method being a modified viscose process. This process, in the course of which small quantities of $CS_2$ are added to an α(1→3)-glucan-containing sodium hydroxide solution, can be used to produce a viscose-like fiber. At the most, 30% of $CS_2$, related to the fiber-forming substance, are used, preferably less than 25% of $CS_2$, and more preferably less than 15% of $CS_2$. Preferably, a quantity between 5 and 30% by weight of $CS_2$, calculated relative to the fiber-forming material, is used, more preferably between 5 and 25%, and most preferably between 5 and 15%. For the purposes of the present invention, such a fiber shall also be referred to as a viscose fiber even though, instead of cellulose, it contains another fiber-forming polysaccharide, namely, said α(1→3)-glucan.

Surprisingly, it was discovered that, unlike in the case of cellulose, in this modified process $CS_2$ is not needed for dissolving the polysaccharide in an aqueous sodium hydroxide solution, but only for slowing down the formation of filaments in the spin bath.

According to the invention, the concentration of NaOH in the spinning solution is to be between 4.0 and 5.5% by weight, calculated relative to the total quantity of the spinning solution. Outside this range, the solubility of the glucan is not sufficient.

For the purposes of the present invention, the term "fiber" shall comprise both staple fibers having a defined staple length and continuous filaments. All principles of the invention that are described hereinafter generally apply to both staple fibers and continuous filaments.

The single fiber titer of the inventive fibers can be between 0.1 and 10 dtex. Preferably, it is between 0.5 and 6.5 dtex, and more preferably between 0.9 and 6.0 dtex. In the case of staple fibers, the staple length is usually between 0.5 and 120 mm, preferably between 20 and 70 mm, and more preferably between 35 and 60 mm. In the case of continuous filaments, the number of individual filaments in the filament yarn is between 50 and 10,000, preferably between 50 and 3,000.

The α(1→3)-glucan can be prepared by bringing an aqueous solution of saccharose into contact with glucosyl-transferase (GtfJ) isolated from *Streptococcus salivarius* (Simpson et al., Microbiology, vol. 41, pp 1451-1460 (1995)).

In a preferred embodiment of the method according to the invention, at least 90% of the α(1→3)-glucan are hexose units and at least 50% of the hexose units are linked via α(1→3)-glycosidic bonds.

The method for the production of the inventive fiber consists of the following steps:
1. Preparing an α(1→3)-glucan solution in a diluted aqueous sodium hydroxide solution.
2. Adding and admixing $CS_2$, brief post-ripening, filtering, and deaerating of the spinning solution.
3. Extruding the α(1→3)-glucan-containing spinning solution through a spinneret into a sulfuric acid spin bath, stretching the fibers, and post-treatment.

The concentration of the fiber-forming substance in the spinning solution can be between 4 and 18% by weight, preferably it is between 4.5 and 15% by weight.

The degree of polymerization of the α(1→3) glucan employed in the method according to the invention, expressed as weight average $DP_W$, can be between 200 and 2000; values between 500 and 1000 are preferred.

A viscose or modal fiber that contains cellulose and α(1→3)-glucan is also the subject-matter of the present invention.

In a preferred embodiment, at least 90% of the α(1→3)-glucan of the inventive viscose fiber are hexose units and at least 50% of the hexose units are linked via α(1→3)-glycosidic bonds.

The use of the inventive fibers for the production of various dry-laid and wet-laid papers, nonwovens, hygiene articles such as tampons, panty liners, and diapers, and other nonwovens, especially absorbent nonwoven products, but also of textile products such as yarns, woven fabrics, or knitted fabrics is also the subject-matter of the present invention.

The invention will be described below with reference to examples. However, the invention is not expressly limited to these examples but also includes all other embodiments that are based on the same inventive concept.

EXAMPLES

The degree of polymerization of the α(1→3)-glucans was determined by means of GPC in DMAc/LiCl. Subsequently, it is always the weight average of the degree of polymerization ($DP_w$) that is specified.

Example 1

An aqueous glucan solution containing 9.1% of α(1→3)-glucan with a $DP_W$ of 800 as well as 4.5% by weight of NaOH was reacted with 7.5% of $CS_2$ (percent by weight calculated relative to the fiber-forming material). The viscose obtained in this way contained 9% by weight of fiber-forming material, 4.5% by weight of NaOH, and 0.57% by weight of sulfur. By using a spinneret, the solution was extruded into a regeneration bath containing 100 g/l of sulfuric acid, 330 g/l of sodium sulfate, and 35 g/l of zinc sulfate. The spinneret had 1053 perforations with a diameter of 50 µm. 2.5% by weight of a nitrogen-containing auxiliary agent (Leomin AC80) were added to the viscose spinning solution. In order to achieve adequate fiber strength, stretching by approx. 75% was carried out in the second bath (92° C., 15 g/l of $H_2SO_4$). The draw-off velocity was 30 m/min.

The properties of the obtained fibers are listed in Table 1.

Example 2

An aqueous glucan solution containing 11% of α(1→3)-glucan with a $DP_W$ of 1000 as well as 4.8% by weight of NaOH was reacted with 15% of $CS_2$ (percent by weight calculated relative to the fiber-forming material). The viscose obtained in this way contained 10.8% by weight of fiber-forming material, 4.7% by weight of NaOH, and 1.37% by weight of sulfur. By using a spinneret, the solution was extruded into a regeneration bath containing 100 g/l of sulfuric acid, 330 g/l of sodium sulfate, and 45 g/l of zinc sulfate. The spinneret had 1053 perforations with a diameter of 50 µm. 3% by weight of a nitrogen-containing auxiliary agent were added to the viscose spinning solution. In order to achieve adequate fiber strength, stretching by approx. 75% was carried out in the second bath (92° C., 15 g/l of $H_2SO_4$). The draw-off velocity was 25 m/min. The properties of the obtained fibers are listed in Table 1.

Example 3

An aqueous glucan solution containing 12.5% of α(1→3)-glucan with a $DP_W$ of 800 as well as 4.4% by weight of NaOH was reacted with 12% of $CS_2$ (percent by weight calculated relative to the fiber-forming material). The viscose obtained in this way contained 12.3% by weight of fiber-forming material, 4.3% by weight of NaOH, and 1.24% by weight of sulfur. By using a spinneret, the solution was extruded into a regeneration bath containing 90 g/l of sulfuric acid, 330 g/l of sodium sulfate, and 45 g/l of zinc sulfate. The spinneret had 1053 perforations with a diameter of 50 µm. 1% by weight of a nitrogen-containing auxiliary agent was added to the viscose spinning solution. In order to achieve adequate fiber strength, stretching by approx. 75% was carried out in the second bath (92° C., 15 g/l of $H_2SO_4$).

The draw-off velocity was 27 m/min. The properties of the obtained fibers are listed in Table 1.

TABLE 1

| example | titer dtex | FFk cN/tex | FDk % |
|---|---|---|---|
| ex. 1 | 1.7 | 17.3 | 19.1 |
| ex. 2 | 1.3 | 23.4 | 16.3 |
| ex. 3 | 1.5 | 21.8 | 18.1 |

FFk fiber strength, conditioned
FDk fiber elongation, conditioned

What is claimed is:

1. A method of producing a polysaccharide fiber whose fiber-forming substance is α(1→3)-glucan, wherein the method comprises:
    (i) preparing a spinning solution comprising α(1→3)-glucan, sodium hydroxide, and carbon disulfide ($CS_2$), wherein there is about 5% to about 7.5% by weight $CS_2$ relative to the α(1→3)-glucan, and
    (ii) extruding the spinning solution to produce the polysaccharide fibers.

2. The method according to claim 1, wherein at least 90% of the α(1→3)-glucan are hexose units and at least 50% of the hexose units are linked via α(1→3)-glycosidic bonds.

3. The method according to claim 1, wherein the fiber is a staple fiber or a continuous filament.

4. The method according to claim 1, wherein step (i) comprises first preparing a solution comprising the α(1→3)-glucan and the sodium hydroxide, and then admixing the $CS_2$ to prepare the spinning solution.

5. The method according to claim 1, further comprising (iii) stretching the polysaccharide fiber.

6. The method according to claim 1, wherein the weight-average degree of polymerization (DPw) of the α(1→3)-glucan is between 200 and 2000.

7. The method according to claim 6, wherein the DPw of the α(1→3)-glucan is between 500 and 1000.

* * * * *